United States Patent [19]

Amick

[11] 4,166,725
[45] Sep. 4, 1979

[54] OIL-SOLUBLE BIOCIDE COMBINATION FOR DISTILLATE FUELS

[75] Inventor: James W. Amick, Highland, Ind.

[73] Assignee: Standard Oil Company (Indiana), Chicago, Ill.

[21] Appl. No.: 514,496

[22] Filed: Oct. 15, 1974

[51] Int. Cl.$^2$ ............................................... C10L 1/22
[52] U.S. Cl. ......................................................... 44/72
[58] Field of Search ....................................... 44/72, 76

[56] References Cited

U.S. PATENT DOCUMENTS

| | | | |
|---|---|---|---|
| 3,044,864 | 7/1962 | Ryder | 44/72 |
| 3,347,646 | 10/1967 | DeGray et al. | 44/76 |
| 3,719,458 | 3/1973 | Cadorette et al. | 44/72 |

Primary Examiner—Winston A. Douglas
Assistant Examiner—Y. Harris-Smith
Attorney, Agent, or Firm—Frank J. Sroka; Arthur G. Gilkes; William T. McClain

[57] ABSTRACT

An improved hydrocarbon fuel composition boiling in the range from about 70° F. to about 750° F., having bactericidal and fungicidal properties, contains from about 0.0005 to about 0.05 weight percent of one or more oil-soluble boron compounds having biocidal properties and from about 0.0005 to about 0.05 weight percent of one or more oil-soluble amine compounds having biocidal properties.

1 Claim, No Drawings

OIL-SOLUBLE BIOCIDE COMBINATION FOR DISTILLATE FUELS

BACKGROUND OF THE INVENTION

It is well known that hydrocarbon fuels when kept in storage vessels such as at oil refineries, distribution terminals, and in smaller fuel tanks almost invariably contain small amounts of water. Some species of bacteria and fungi normally found in soil and ground water have been found also to exist in this water, deriving their nutrition from the hydrocarbon phase as well as from trace elements found in the water. This metabolism is responsible for the consumption of some amount of petroleum product, tank corrosion, and general product deterioration by forming rust, hydrogen sulfide, gums and filamentous material at the interface between the water and the hydrocarbon.

Petroleum refining and marketing companies have modern storage and distribution facilities to assure distillate fuel users that their products will normally be free of excessive particulate matter and dispersed water. However, many incidents in recent years have demonstrated that maintaining strict standards of fuel cleanliness is not adequate. Severe operational difficulties can be encountered when distillate fuels contain minute traces of microbial contamination. These operational problems have been reported by domestic heating oil suppliers, railroads, commercial airlines and at military installations.

The finished fuels as produced by petroleum refiners are essentially microbe-free. However, in normal fuel distribution and storage microbial populations can increase significantly. The microorganisms can originate from rain water draining through the fuel in a floating roof tank, soil or drain water entering tanks through fill pipes or leaks, dust particles entering working fuel tanks through vents, and harbor waters used in ballasting marine tankers.

Microscopic organisms have been found growing in many distillate fuel facilities. Bacteria and fungi have been the microorganisms observed in the greatest numbers. A complete bacterium is a simple cell of perhaps only 0.5 micron in diameter. Influenced by environmental conditions these may aggregate into scums at fuel-water interfaces or into macroscopic clumps in the fuel or water phases of fuel tanks, pipe lines, or filters.

Motor fuel or gasoline generally boils from about 70° F. to about 450° F. For many years tetraalkyl lead compounds have been used in gasoline to improve octane quality. These lead compounds were also effective at inhibiting the growth of bacteria. Bacteria are generally present in fuel storage tank water bottoms and can grow rapidly in a light hydrocarbon fuel in the absence of an effective biocide or growth inhibitor.

But currently, air quality measures are directed toward the removal of lead compounds from motor fuels and unleaded gasolines can be expected to be marketed in increasing volumes. Unfortunately these unleaded fuels are susceptible to bacterial and fungicidal growth. This growth can proceed to the point where the bacteria and fungi can cause fuel filter plugging in automobiles.

Heating oils such as kerosene which boils from about 325° F. to about 550° F., and furnace oil, which boils from about 350° F. to about 700° F. are subject to microbiological growth. This growth usually exists in the form of brown or black sludge or slime at the water-oil interface in storage tanks. Not only does this growth get swept up into the fuel to cause plugging in furnace filters, but the growth also produces surfactants which cause excessive water and particulate matter to become suspended in the oil, leading to fuel filter plugging and burner nozzle coking. Microbiological sludges in home heating oil tanks can even interfere with the operation of tank floats and fill whistles.

Jet fuels such as JP-4 and Type A are also susceptible to microbial contamination and many incidents have been reported where microorganisms have caused serious operational difficulties. The contamination not only leads to shorter filter life in the ground handling of jet fuel, but can also have adverse affects on aircraft operation. Serious corrosion of aluminum alloys in integral wing tanks has been linked to microbiological growth and the surfactants and water associated with it.

Filter plugging is a particularly serious problem in aircraft because of the consequences of operational failure. Moreover, the tendency toward filter plugging in jet engines is aggrevated due to the large volume of fuel consumed. At these high volumes, a low concentration of contaminants can quickly become a troublesome amount of residue in the filter system of the engine.

It is the primary objective of the present invention to provide a biocidal agent which is fuel-soluble so that it is carried along as fuel is transferred from one storage vessel to another. In this manner effective control of microbiological growth may be accomplished by adding the agent to fuel at a single point in the distribution system. For example, addition of the biocide to furnace oil at a bulk plant would prevent microbiological growth at the bulk plant and also at storage areas downstream such as home storage tanks. Addition of biocide at a distribution terminal would provide protection at the terminal and at downstream areas such as bulk plants and home storage areas. Naturally treatment at the refinery would provide the broadest protection. But at times it is considered economically more prudent to treat that level of the distribution system which is experiencing microbiological activity, thereby also treating the distribution system downstream of it.

The use of fuel-soluble boron compounds as biocides has been known for quite some time. Canadian Pat. No. 642,919 claims the use of organoborates to prevent microbial degradation of petroleum. The compounds claimed are condensation products of an alkali metal borate and ethylene glycol, diethylene glycol, triethylene glycol, 1,4-butanediol, 2,3-butanediol, and 1,2-propanediol. Canadian Pat. No. 648,972 and U.S. Pat. No. 3,347,646 teach the use of fuel soluble biocides having the following general formula:

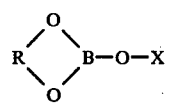

in which X is selected from the group consisting of hydrogen,

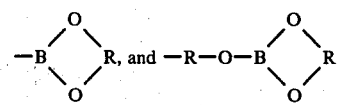

wherein R is an alpha or beta alkylene radical containing from 3 to about 12 carbon atoms.

Various amine compounds are known to be effective biocides. For example, U.S. Pat. No. 3,719,458 teaches the use of fuel soluble biocides having the formula:

in which R is an alkyl radical having from one to four carbon atoms and R' is hydrogen or an alkyl radical having from one to four carbon atoms. Other diamines, such as long chain alkyl substituted 1, 3 propanediamines, are also known to have biocidal activity. An example of one such compound is Duomeen L-11 which has the following formula:

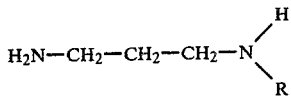

where R is an alkyl group having an average chain length of 11 carbon atoms. A number of other amines are known to have bacteriological and fungicidal properties.

A biocide is needed for distillate fuels that will kill a broad spectrum of microorganisms. Biobor JF, a commercial biocide, has been used in some cases to control microbiological growth. Biobor JF contains 5 percent petroleum naphtha and 95 percent of a mixture of 2,2'-oxybis (4,4,6-trimethyl-1,3,2-dioxaborinane) and 2,2'-(1-methyltrimethylenedioxy) bis-(4-methyl-1,3,2-dioxaborinane). This additive has been used in a concentration range of 25 to 300 ppm, but preferably 50 to 175 ppm.

SUMMARY OF THE INVENTION

This invention relates to a hydrocarbon fuel composition adapted to provide bactericidal and fungicidal activity and a method for providing such activity. More specifically, the distillate hydrocarbon fuel composition of the invention comprises a major portion of a mixture of hydrocarbons boiling in the range from about 70° F. to about 750° F. containing a minor amount of one or more oil-soluble boron compounds having biocidal properties and one or more oil-soluble amine compounds having biocidal properties.

It has been observed that a single biocide sometimes cannot adequately control the broad spectrum of bacteria and fungi present in fuel storage tanks and distribution systems. We have found that combinations of biocides not only provide a broad spectrum kill of microorganisms but also provide better microbiological control than would be expected from such a combination. Such activity results in better protection against microorganisms and reduced additive treatment costs.

The combinations of biocides of this invention comprise one or more oil soluble boron compounds having biocidal properties and one or more oil-soluble amine compounds having biocidal properties. The boron compound component may be any oil-soluble boron compound having biocidal properties. Some boron compounds which are encompassed by this invention are condensation products of an alkali metal borate and ethylene glycol, diethylene glycol, triethylene glycol, 1,4-butanediol, 2,3-butanediol, and 1,5-propanediol. Some boron compounds which are encompassed by this invention have the following general formula:

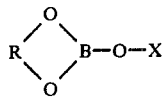

in which X is selected from the group consisting of hydrogen,

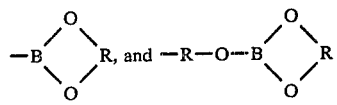

where R is an alpha or beta alkylene radical containing from 2 to about 12 carbon atoms. Other oil-soluble boron compounds of various other chemical structures having biocidal activity are also encompassed by this invention.

The amine compound component may be any oil-soluble amine compound having biocidal properties. Included within this group of compounds are various alkyl and aryl substituted mono-amines and various alkyl and aryl substituted di-amines. Some amine compounds which are encompassed by this invention have the following general formula:

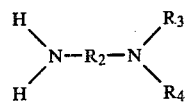

wherein $R_2$ is a $C_1$–$C_4$ alkyl group, and $R_3$ and $R_4$ are selected from the group consisting of hydrogen and $C_1$–$C_{30}$ alkyl groups. $R_3$ may be hydrogen and $R_4$ may be $C_6$–$C_{24}$ alkyl groups. Other oil-soluble amine compounds of various other chemical structures having biocidal activity are also encompassed by this invention.

The biocidal agents of this invention should be used in concentrations that are effective to destroy microorganisms, i.e. in microbicidal proportion. The optimum concentration of the biocidal agents of this invention may, of course, vary with the degree of microorganism infection of the fuel and/or water associated therewith. In general, effective results will be obtained by using each biocidal agent of the kind disclosed herein in amounts between about 0.0005 and about 0.05 percent. Normally concentrations of about 0.001 to about 0.025 will be preferred so as to obtain a good balance between economy and effectiveness of results. In individual instances where microorganism infection is at a low level, concentrations of the biocidal agents as low as 0.0005 percent can be used. On the other hand, where a relatively high level of infection exists, concentrations of biocidal agents as high as 0.05 percent may be desirable.

The hydrocarbon fuel composition of the invention consists of any light distillate hydrocarbon fraction boiling in the gasoline through middle distillate boiling ranges. The base fuel may consist of paraffinic, naphahenic and/or aromatic hydrocarbons or mixtures thereof. The base fuels are obtained from the distillation of crude oil by the catalytic or thermal cracking of gas oils, by the alkylation of isoparaffins with olefins, or by the polymerization of olefins. The boiling range of the base fuel will generally be in the range from 70° F. to 750° F. Motor fuel or gasoline generally boils from about 70° to 450° F., kerosene and turbine fuel generally boil from about 325° to 575° F. and diesel fuel and furnace oil generally boil from about 350° to 700° F. The base fuel composition may also contain additives conventionally employed in gasoline or distillates such as anti-oxidants, stabilizers, dyes, anti-icing additives and the like.

Our invention is exemplified by the following test.

EXAMPLE

Biocide effectiveness was determined by subjecting a treated fuel to a microorganism growth test. In this test, 1500 ml of a distillate fuel, 10 ml of Bushnell-Haas solution, and 3 ml of an inoculating solution are kept in the dark at room temperature for 40 days. The Bushnell-Haas solution is an aqueous solution which provides nutrients such as nitrogen, phosphorus and potassium for microbiological growth. The inoculating solution is water bottoms from fuel oil storage tanks which were encountering microbiological growth. At the end of the growth period, the oil-water interface was inspected for growth which was generally attributable to fungi. A bacteria count was also made on the water phase by the Panatest method.

The test results are set forth in the table below:

Table I

| Fuel Composition | Growth Test Appearance | Bacteria Count |
|---|---|---|
| Fuel A | heavy fungi | $10^4$–$10^5$ |
| Fuel A + 20 ppm Duomeen L-11 | no fungi | 1–$10^3$ |
| Fuel A + 100 ppm Biobor JF | heavy fungi | 1–$10^3$ |
| Fuel A + 150 ppm Biobor JF | heavy fungi | 1–$10^3$ |
| Fuel A + 20 ppm Duomeen L-11 + 100 ppm Biobor JF | no fungi | 0 |

Fuel A was a furnace oil made up of a mixture of straight run and cracked distillate boiling in the range of 350° F. to 620° F.

After the 40 day storage period, untreated fuel experienced a heavy growth of both fungi and bacteria. Treatment with 20 ppm of Duomeen L-11 completely controlled fungi but only partially controlled bacteria growth. Treatment with 100 ppm Biobor JF partially controlled bacteria but had little effect on fungi. Increasing the Biobor JF concentration to 150 ppm did not improve biocidal protection. But the mixture of 20 ppm Duomeen L-11 and 100 ppm Biobor JF completely controlled both fungi and bacteria. This complete control cannot be accounted for by the addition of the effectiveness of each individual component of the mixture.

While 150 ppm Biobor JF provided some bactericidal protection and very little fungicidal protection, the mixture of 100 ppm Biobor JF and 20 ppm Duomeen L-11 provided complete fungicidal and bactericidal protection. The mixture was more effective at lower cost.

This example demonstrates that mixtures of various oil-soluble biocides can be highly effective in controlling microbiological growth.

I claim:

1. A fuel composition having biocidal properties comprising a major proportion of hydrocarbon fuel boiling in the range from about 70° F. to about 750° F., about 0.0005 to about 0.05 weight percent of a mixture of 2,2'-oxybis(4,4,6-trimethyl-1,3,2-dioxaborinane) and 2,2'-(1-methyl-trimethylene dioxy)bis-(4-methyl-1,3,2-dioxaborinane), and about 0.0005 to about 0.05 weight percent of a compound having the formula

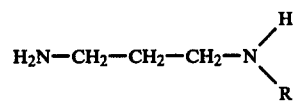

where R is an alkyl group having an average chain length of 11 carbon atoms.

* * * * *